(12) United States Patent
Borg et al.

(10) Patent No.: US 7,604,660 B2
(45) Date of Patent: Oct. 20, 2009

(54) BIFURCATED MEDICAL APPLIANCE DELIVERY APPARATUS AND METHOD

(75) Inventors: Ulf R Borg, Cornelius, NC (US); Eric K Mangiardi, Charlotte, NC (US); Jason R Reynolds, Charlotte, NC (US)

(73) Assignee: Merit Medical Systems, Inc., South Jordan, UT (US)

( * ) Notice: Subject to any disclaimer, the term of this patent is extended or adjusted under 35 U.S.C. 154(b) by 137 days.

(21) Appl. No.: 10/427,539

(22) Filed: May 1, 2003

(65) Prior Publication Data
US 2004/0220653 A1 Nov. 4, 2004

(51) Int. Cl.
*A61F 2/06* (2006.01)
*A61F 11/00* (2006.01)
(52) U.S. Cl. .................. 623/1.11; 606/108
(58) Field of Classification Search ............ 623/1.11, 623/1.15; 606/108, 191, 194, 195
See application file for complete search history.

(56) References Cited

U.S. PATENT DOCUMENTS

| | | | |
|---|---|---|---|
| 3,196,876 | A | 7/1965 | Roberts et al. |
| 4,343,048 | A | 8/1982 | Ross et al. |
| 4,606,330 | A | 8/1986 | Bonnet |
| 4,665,906 | A | 5/1987 | Jervis |
| 4,680,031 | A | 7/1987 | Alonso |
| 4,733,665 | A | 3/1988 | Palmaz |
| 4,739,762 | A | 4/1988 | Palmaz |
| 4,820,262 | A | 4/1989 | Finney |
| 4,893,623 | A | 1/1990 | Rosenbluth |
| 5,019,085 | A | 5/1991 | Hillstead |
| 5,032,128 | A | 7/1991 | Alonso |
| 5,067,957 | A | 11/1991 | Jervis |

(Continued)

FOREIGN PATENT DOCUMENTS

DE 199 06 956 A 1 8/2000

(Continued)

OTHER PUBLICATIONS

International Search Report, PCT International Search Report mailed ()Sep. 29, 2005 for PCT/US2004/09678 (Filed Mar. 30, 2004).

(Continued)

*Primary Examiner*—Vy Q. Bui
(74) *Attorney, Agent, or Firm*—Alston & Bird LLP

(57) ABSTRACT

The present invention, in preferred embodiments, provides delivery and deployment apparatuses for bifurcated stents capable of comfortably cradling the corina of bifurcated target tissue between the arms of the bifurcated stent as each arm of the bifurcated stent is delivered to a respective side branch. In particular, a family of apparatuses is provided that may be indicated for vascular and non-vascular intervention. Additionally, these apparatuses do not require the use of an ancillary means, such as one or more balloon catheters to achieve complete and precise deployment. In preferred embodiments, delivery and deployment devices in accordance with the present invention also provide, direct visualization, deployment safety features and enhanced physician control.

18 Claims, 9 Drawing Sheets

U.S. PATENT DOCUMENTS

| | | |
|---|---|---|
| 5,073,694 A | 12/1991 | Tessier et al. |
| 5,102,417 A | 4/1992 | Palmaz |
| 5,104,404 A | 4/1992 | Wolff |
| 5,159,920 A | 11/1992 | Condon et al. |
| 5,190,546 A | 3/1993 | Jervis |
| 5,195,984 A | 3/1993 | Schatz |
| 5,249,585 A | 10/1993 | Turner et al. |
| 5,292,331 A | 3/1994 | Boneau |
| 5,320,617 A | 6/1994 | Leach |
| 5,345,057 A | 9/1994 | Muller |
| 5,354,309 A | 10/1994 | Schnepp-Pesch et al. |
| 5,356,423 A | 10/1994 | Tihon et al. |
| 5,383,892 A | 1/1995 | Cardon et al. |
| 5,409,453 A | 4/1995 | Lundquist et al. |
| 5,421,955 A | 6/1995 | Lau et al. |
| 5,443,498 A | 8/1995 | Fontaine |
| 5,449,373 A | 9/1995 | Pinchasik et al. |
| 5,514,093 A | 5/1996 | Ellis et al. |
| 5,514,154 A | 5/1996 | Lau et al. |
| 5,549,644 A | 8/1996 | Lundquist et al. |
| 5,588,949 A | 12/1996 | Taylor et al. |
| 5,591,157 A | 1/1997 | Hennings et al. |
| 5,591,197 A | 1/1997 | Orth et al. |
| 5,593,442 A | 1/1997 | Klein |
| 5,597,378 A | 1/1997 | Jervis |
| 5,601,591 A | 2/1997 | Edwards et al. |
| 5,603,698 A | 2/1997 | Roberts et al. |
| 5,643,312 A | 7/1997 | Fischell et al. |
| 5,667,522 A | 9/1997 | Flomenbilt et al. |
| 5,669,924 A | 9/1997 | Shaknovich |
| 5,681,346 A | 10/1997 | Orth et al. |
| 5,690,644 A | 11/1997 | Yurek et al. |
| 5,695,499 A | 12/1997 | Helgrson et al. |
| 5,702,418 A | 12/1997 | Ravenscroft |
| 5,707,386 A | 1/1998 | Schnepp-Pesch et al. |
| 5,716,393 A | 2/1998 | Lindenberg et al. |
| 5,733,303 A | 3/1998 | Israel et al. |
| 5,746,692 A | 5/1998 | Bacich et al. |
| 5,755,776 A | 5/1998 | Al-Saadon |
| 5,759,192 A | 6/1998 | Saunders |
| 5,766,238 A | 6/1998 | Lau et al. |
| 5,776,161 A | 7/1998 | Globerman |
| 5,780,807 A | 7/1998 | Saunders |
| 5,782,838 A | 7/1998 | Beyar et al. |
| 5,803,080 A | 9/1998 | Freitag |
| 5,807,404 A | 9/1998 | Richter |
| 5,814,063 A | 9/1998 | Freitag |
| 5,817,102 A | 10/1998 | Johnson et al. |
| 5,824,058 A | 10/1998 | Ravenscroft et al. |
| 5,833,694 A | 11/1998 | Poncet |
| 5,836,966 A | 11/1998 | St. Germain |
| 5,843,120 A | 12/1998 | Israel et al. |
| 5,860,999 A | 1/1999 | Schnepp-Pesch et al. |
| 5,876,448 A | 3/1999 | Thompson et al. |
| 5,876,449 A | 3/1999 | Starck et al. |
| 5,879,370 A | 3/1999 | Fischell et al. |
| 5,902,333 A | 5/1999 | Roberts et al. |
| 5,902,475 A | 5/1999 | Trozera et al. |
| 5,911,732 A | 6/1999 | Hojeibane |
| 5,922,020 A | 7/1999 | Klein et al. |
| 5,935,162 A | 8/1999 | Dang |
| 5,972,018 A | 10/1999 | Israel et al. |
| 5,980,552 A | 11/1999 | Pinchasik et al. |
| 5,984,964 A | 11/1999 | Roberts et al. |
| 6,017,365 A | 1/2000 | Von Oepen |
| 6,019,778 A | 2/2000 | Wilson et al. |
| 6,022,371 A | 2/2000 | Killion |
| 6,033,435 A | 3/2000 | Penn et al. |
| 6,042,597 A | 3/2000 | Kveen et al. |
| 6,048,361 A | 4/2000 | Von Oepen |
| 6,051,021 A | 4/2000 | Frid |
| 6,053,941 A | 4/2000 | Lindenberg et al. |
| 6,056,775 A | 5/2000 | Borghi et al. |
| 6,059,811 A | 5/2000 | Pinchasik et al. |
| 6,086,528 A | 7/2000 | Adair |
| 6,099,560 A | 8/2000 | Penn et al. |
| 6,131,266 A | 10/2000 | Saunders |
| 6,132,461 A | 10/2000 | Thompson |
| 6,136,006 A | 10/2000 | Johnson et al. |
| 6,146,403 A | 11/2000 | St. Germain |
| 6,156,035 A | 12/2000 | Songer |
| 6,156,052 A | 12/2000 | Richter et al. |
| 6,162,231 A | 12/2000 | Mikus et al. |
| 6,179,867 B1 | 1/2001 | Cox |
| 6,203,568 B1 | 3/2001 | Lombardi et al. |
| 6,217,608 B1 | 4/2001 | Penn et al. |
| 6,221,102 B1 | 4/2001 | Baker et al. |
| 6,238,430 B1 | 5/2001 | Klumb et al. |
| 6,254,609 B1 | 7/2001 | Vrba et al. |
| 6,261,316 B1 * | 7/2001 | Shaolian et al. ............ 623/1.11 |
| 6,299,622 B1 | 10/2001 | Snow et al. |
| 6,302,906 B1 | 10/2001 | Goicoechea et al. |
| 6,306,141 B1 | 10/2001 | Jervis |
| 6,315,794 B1 | 11/2001 | Richter |
| 6,322,586 B1 | 11/2001 | Monroe et al. |
| 6,325,790 B1 | 12/2001 | Trotta |
| 6,369,355 B1 | 4/2002 | Saunders |
| 6,375,676 B1 | 4/2002 | Cox |
| 6,380,457 B1 | 4/2002 | Yurek et al. |
| 6,423,084 B1 | 7/2002 | St. Germain |
| 6,428,570 B1 | 8/2002 | Globerman |
| 6,440,161 B1 | 8/2002 | Madrid et al. |
| 6,440,162 B1 | 8/2002 | Cox et al. |
| 6,443,982 B1 | 9/2002 | Israel et al. |
| 6,451,025 B1 | 9/2002 | Jervis |
| 6,454,789 B1 | 9/2002 | Chen et al. |
| 6,461,381 B2 | 10/2002 | Israel et al. |
| 6,464,720 B2 | 10/2002 | Boatman et al. |
| 6,464,722 B2 | 10/2002 | Israel et al. |
| 6,488,697 B1 | 12/2002 | Ariura et al. |
| 6,508,834 B1 | 1/2003 | Pinchasik et al. |
| 6,514,245 B1 | 2/2003 | Williams et al. |
| 6,514,281 B1 | 2/2003 | Blaeser et al. |
| 6,514,285 B1 | 2/2003 | Pinchasik |
| 6,517,558 B2 | 2/2003 | Gittings et al. |
| 6,517,569 B2 | 2/2003 | Mikus et al. |
| 6,533,805 B1 | 3/2003 | Jervis |
| 6,540,777 B2 | 4/2003 | Stenzel |
| 6,558,396 B1 | 5/2003 | Inoue |
| 6,569,085 B2 | 5/2003 | Kortenbach et al. |
| 6,569,194 B1 | 5/2003 | Pelton |
| 6,572,646 B1 | 6/2003 | Boylan et al. |
| 6,589,276 B2 | 7/2003 | Pinchasik et al. |
| 6,607,551 B1 | 8/2003 | Sullivan et al. |
| 6,613,078 B1 | 9/2003 | Barone |
| 6,620,193 B1 | 9/2003 | Lau et al. |
| 6,623,491 B2 | 9/2003 | Thompson |
| 6,635,084 B2 | 10/2003 | Israel et al. |
| 6,638,300 B1 | 10/2003 | Frantzen |
| 6,641,608 B1 | 11/2003 | Pulnev |
| 6,641,609 B2 | 11/2003 | Globerman |
| 6,645,242 B1 | 11/2003 | Quinn |
| 6,652,573 B2 | 11/2003 | von Oepen |
| 6,652,575 B2 | 11/2003 | Wang |
| 6,656,201 B2 | 12/2003 | Ferrera et al. |
| 6,656,211 B1 | 12/2003 | DiCaprio |
| 6,656,214 B1 | 12/2003 | Fogarty et al. |
| 6,660,034 B1 | 12/2003 | Mandrusov et al. |
| 6,663,660 B2 | 12/2003 | Dusbabek et al. |
| 6,663,664 B1 | 12/2003 | Pacetti |
| 6,663,880 B1 | 12/2003 | Roorda et al. |
| 6,666,881 B1 | 12/2003 | Richter et al. |
| 6,666,884 B1 | 12/2003 | Webster |
| 6,669,716 B1 | 12/2003 | Gilson et al. |

| Patent | Date | Inventor |
|---|---|---|
| 6,669,718 B2 | 12/2003 | Besselink |
| 6,669,720 B1 | 12/2003 | Pierce |
| 6,669,722 B2 | 12/2003 | Chen et al. |
| 6,669,723 B2 | 12/2003 | Killion et al. |
| 6,673,101 B1 | 1/2004 | Fitzgerald et al. |
| 6,673,104 B2 | 1/2004 | Barry |
| 6,673,107 B1 | 1/2004 | Brandt et al. |
| 6,676,692 B2 | 1/2004 | Rabkin et al. |
| 6,676,693 B1 | 1/2004 | Belding et al. |
| 6,676,697 B1 | 1/2004 | Richter |
| 6,679,910 B1 | 1/2004 | Granada |
| 6,679,911 B2 | 1/2004 | Burgermeister |
| 6,689,157 B2 | 2/2004 | Madrid et al. |
| 6,692,483 B2 | 2/2004 | Vardi et al. |
| 6,692,522 B1 | 2/2004 | Richter |
| 6,695,809 B1 | 2/2004 | Lee |
| 6,695,812 B2 | 2/2004 | Estrada et al. |
| 6,695,833 B1 | 2/2004 | Frantzen |
| 6,695,862 B2 | 2/2004 | Cox et al. |
| 6,695,876 B1 | 2/2004 | Marotta et al. |
| 6,699,274 B2 | 3/2004 | Stinson |
| 6,699,277 B1 | 3/2004 | Freidberg et al. |
| 6,702,849 B1 | 3/2004 | Dutta et al. |
| 6,702,850 B1 | 3/2004 | Byun et al. |
| 6,706,061 B1 | 3/2004 | Fischell et al. |
| 6,706,062 B2 | 3/2004 | Vardi et al. |
| 6,709,440 B2 | 3/2004 | Callol et al. |
| 6,709,451 B1 | 3/2004 | Noble et al. |
| 6,716,240 B2 | 4/2004 | Fischell et al. |
| 6,719,782 B1 | 4/2004 | Chuter |
| 6,723,071 B2 | 4/2004 | Gerdts et al. |
| 6,723,113 B1 | 4/2004 | Shkolnik |
| 6,726,712 B1 | 4/2004 | Raeder-Devens et al. |
| 6,730,116 B1 | 5/2004 | Wolinsky et al. |
| 6,730,117 B1 | 5/2004 | Tseng et al. |
| 6,733,521 B2 | 5/2004 | Chobotov et al. |
| 6,733,523 B2 | 5/2004 | Shaolian et al. |
| 6,736,828 B1 | 5/2004 | Adams et al. |
| 6,740,113 B2 | 5/2004 | Vrba |
| 6,740,114 B2 | 5/2004 | Burgermeister |
| 6,743,219 B1 | 6/2004 | Dwyer et al. |
| 6,746,423 B1 | 6/2004 | Wantink |
| 6,746,475 B1 | 6/2004 | Rivelli, Jr. |
| 6,746,476 B1 | 6/2004 | Hojeibane |
| 6,746,479 B2 | 6/2004 | Ehr et al. |
| 6,749,627 B2 | 6/2004 | Thompson et al. |
| 6,749,629 B1 | 6/2004 | Hong et al. |
| 6,752,819 B1 | 6/2004 | Brady et al. |
| 6,752,825 B2 | 6/2004 | Eskuri |
| 6,755,855 B2 | 6/2004 | Yurek et al. |
| 6,756,007 B2 | 6/2004 | Pletzer et al. |
| 6,761,703 B2 | 7/2004 | Miller et al. |
| 6,761,708 B1 | 7/2004 | Chiu et al. |
| 6,761,731 B2 | 7/2004 | Majercak |
| 6,761,733 B2 | 7/2004 | Chobotov et al. |
| 6,764,505 B1 | 7/2004 | Hossainy et al. |
| 6,764,506 B2 | 7/2004 | Roubin et al. |
| 6,764,519 B2 | 7/2004 | Whitmore, III |
| 6,770,088 B1 | 8/2004 | Jang |
| 6,770,091 B2 | 8/2004 | Richter et al. |
| 6,773,446 B1 | 8/2004 | Dwyer et al. |
| 6,773,447 B2 | 8/2004 | Laguna |
| 6,773,448 B2 | 8/2004 | Kusleika et al. |
| 6,774,157 B2 | 8/2004 | DelMain |
| 6,776,793 B2 | 8/2004 | Brown et al. |
| 6,776,795 B2 | 8/2004 | Pelton |
| 6,780,182 B2 | 8/2004 | Bowman et al. |
| 6,780,199 B2 | 8/2004 | Solar et al. |
| 6,786,918 B1 | 9/2004 | Krivoruchko et al. |
| 6,790,220 B2 | 9/2004 | Morris et al. |
| 6,790,222 B2 | 9/2004 | Kugler et al. |
| 6,790,223 B2 | 9/2004 | Reever |
| 6,790,227 B2 | 9/2004 | Burgermeister |
| 6,796,997 B1 | 9/2004 | Penn et al. |
| 6,800,081 B2 | 10/2004 | Parodi |
| 6,802,846 B2 | 10/2004 | Hauschild et al. |
| 6,802,849 B2 | 10/2004 | Blaeser et al. |
| 6,802,859 B1 | 10/2004 | Pazienza et al. |
| 6,805,702 B1 | 10/2004 | Chen et al. |
| 6,805,704 B1 | 10/2004 | Hoyns |
| 6,805,705 B2 | 10/2004 | Hong et al. |
| 6,805,706 B2 | 10/2004 | Solovay et al. |
| 6,805,707 B1 | 10/2004 | Hong et al. |
| 6,808,529 B2 | 10/2004 | Fulkerson |
| 6,814,748 B1 * | 11/2004 | Baker et al. ................. 623/1.14 |
| 6,843,802 B1 | 1/2005 | Villalobos et al. |
| 6,860,898 B2 | 3/2005 | Stack et al. |
| 6,899,727 B2 | 5/2005 | Armstrong et al. |
| 6,911,039 B2 | 6/2005 | Shiu et al. |
| 6,942,674 B2 | 9/2005 | Belef et al. |
| 6,953,475 B2 | 10/2005 | Shaolian et al. |
| 6,972,054 B2 | 12/2005 | Kerrigan |
| 6,984,244 B2 | 1/2006 | Perez et al. |
| 6,989,024 B2 | 1/2006 | Herbert et al. |
| 7,011,675 B2 | 3/2006 | Hemerick et al. |
| 2001/0007954 A1 | 7/2001 | Shaolian et al. |
| 2001/0016767 A1 | 8/2001 | Wilson et al. |
| 2001/0016768 A1 | 8/2001 | Wilson et al. |
| 2001/0027339 A1 | 10/2001 | Boatman et al. |
| 2001/0037138 A1 | 11/2001 | Wilston et al. |
| 2002/0042650 A1 | 4/2002 | Vardi et al. |
| 2002/0077692 A1 | 6/2002 | Besselink |
| 2002/0111672 A1 | 8/2002 | Kim et al. |
| 2002/0156524 A1 | 10/2002 | Ehr et al. |
| 2002/0161425 A1 | 10/2002 | Hemerick et al. |
| 2002/0183763 A1 | 12/2002 | Callol et al. |
| 2002/0183831 A1 | 12/2002 | Rolando et al. |
| 2002/0183832 A1 | 12/2002 | Penn et al. |
| 2002/0193866 A1 | 12/2002 | Saunders |
| 2002/0198593 A1 | 12/2002 | Gomez et al. |
| 2003/0004567 A1 | 1/2003 | Boyle et al. |
| 2003/0036793 A1 | 2/2003 | Richter et al. |
| 2003/0045925 A1 | 3/2003 | Jayaraman |
| 2003/0050690 A1 | 3/2003 | Kveen et al. |
| 2003/0077310 A1 | 4/2003 | Pathak et al. |
| 2003/0083734 A1 | 5/2003 | Friedrich et al. |
| 2003/0105511 A1 | 6/2003 | Welsh et al. |
| 2003/0105513 A1 | 6/2003 | Moriuchi et al. |
| 2003/0114919 A1 | 6/2003 | McQuiston et al. |
| 2003/0125799 A1 | 7/2003 | Limon |
| 2003/0139796 A1 | 7/2003 | Sequin et al. |
| 2003/0144671 A1 | 7/2003 | Brooks et al. |
| 2003/0144726 A1 | 7/2003 | Majercak et al. |
| 2003/0144731 A1 | 7/2003 | Wolinsky et al. |
| 2003/0149469 A1 | 8/2003 | Wolinsky et al. |
| 2003/0158596 A1 | 8/2003 | Ikeuchi et al. |

FOREIGN PATENT DOCUMENTS

| | | |
|---|---|---|
| DE | 199 37 638 A 1 | 5/2001 |
| EP | 0 350 302 | 1/1990 |
| EP | 0 378 151 A2 | 7/1990 |
| EP | 0 516 189 A1 | 12/1992 |
| EP | 0 540 290 A2 | 5/1993 |
| EP | 0 945 107 A2 | 1/1999 |
| EP | 1 093 771 A2 | 4/2001 |
| EP | 1 208 814 A2 | 9/2001 |
| JP | 2001-299932 | 10/2001 |
| WO | WO 91/13384 | 9/1991 |
| WO | WO 92/11824 | 7/1992 |
| WO | WO 93/22986 | 11/1993 |
| WO | WO 94/21196 | 9/1994 |
| WO | WO 96/14028 | 5/1996 |
| WO | WO 97/14456 | 4/1997 |
| WO | WO 97/40739 | 11/1997 |
| WO | WO 99/62430 | 12/1999 |

| | | |
|---|---|---|
| WO | WO 01/76508 A2 | 10/2001 |
| WO | WO 02/083038 A2 | 10/2002 |

OTHER PUBLICATIONS

International Preliminary Report on Patentability mailed Nov. 17, 2005 for PCT/US2004/09678 (Filed Mar. 30, 2004).

Office Action for Canadian Application No. 2,523,715, completed Oct. 23, 2007, received Oct. 26, 2007.

* cited by examiner

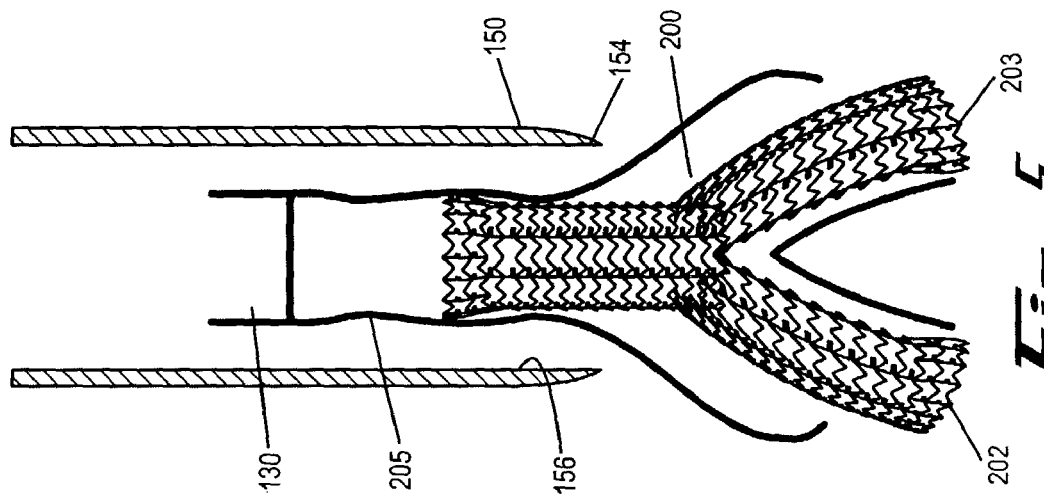
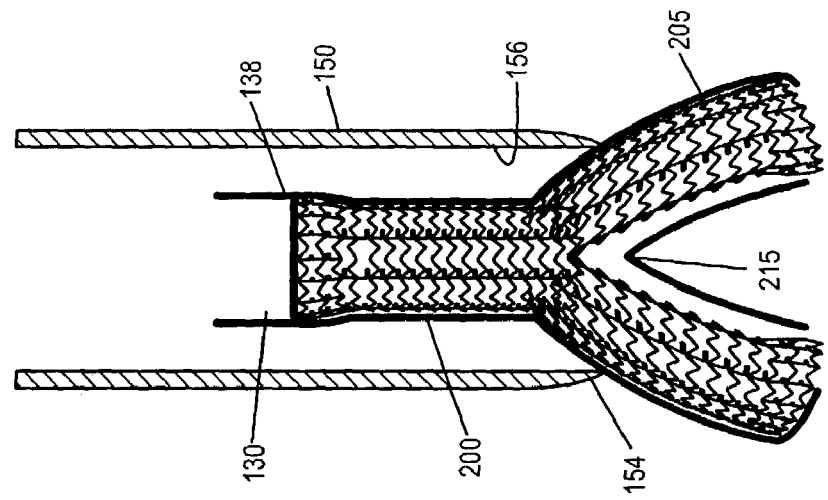
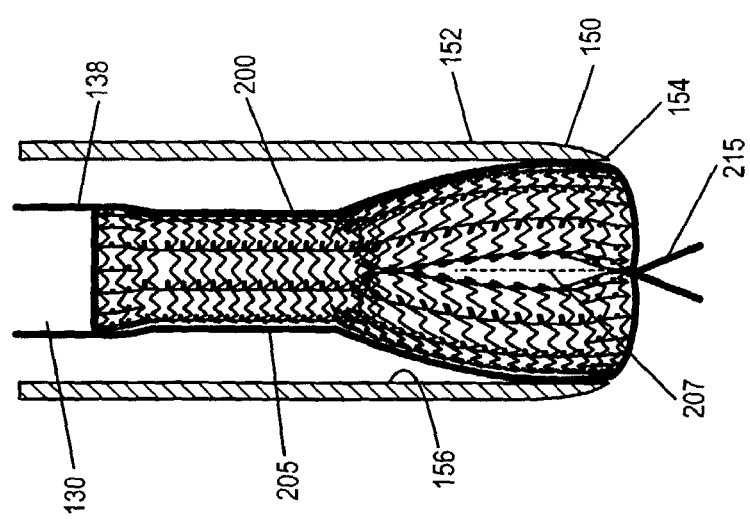

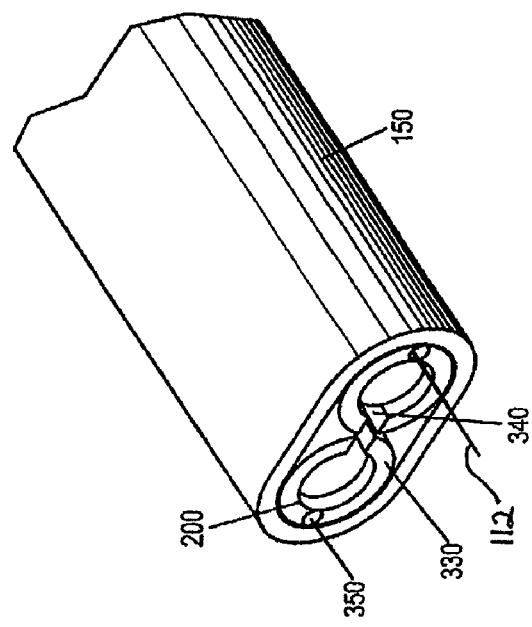
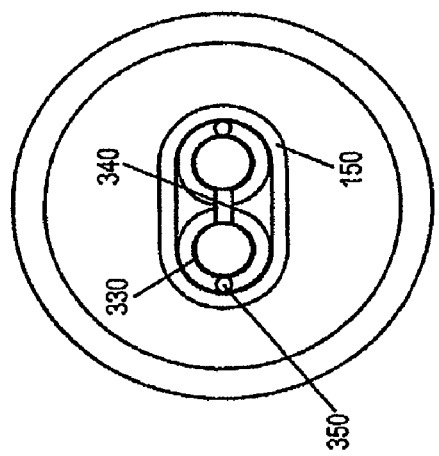
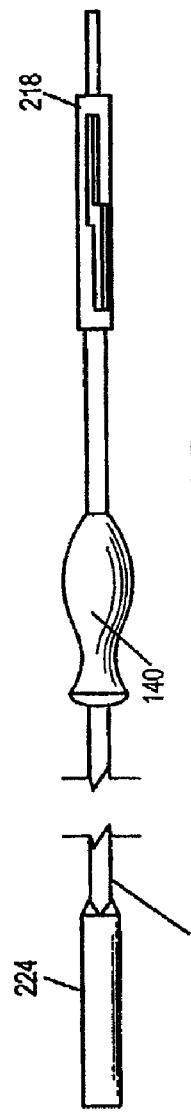

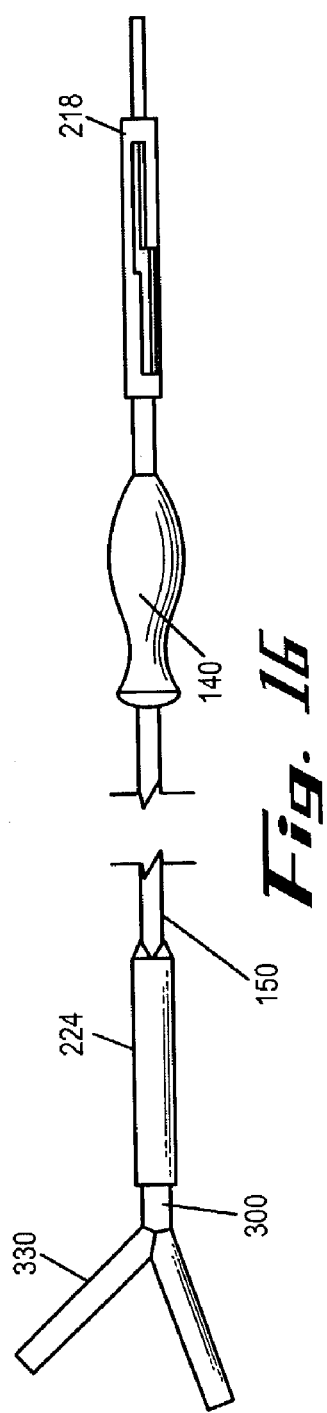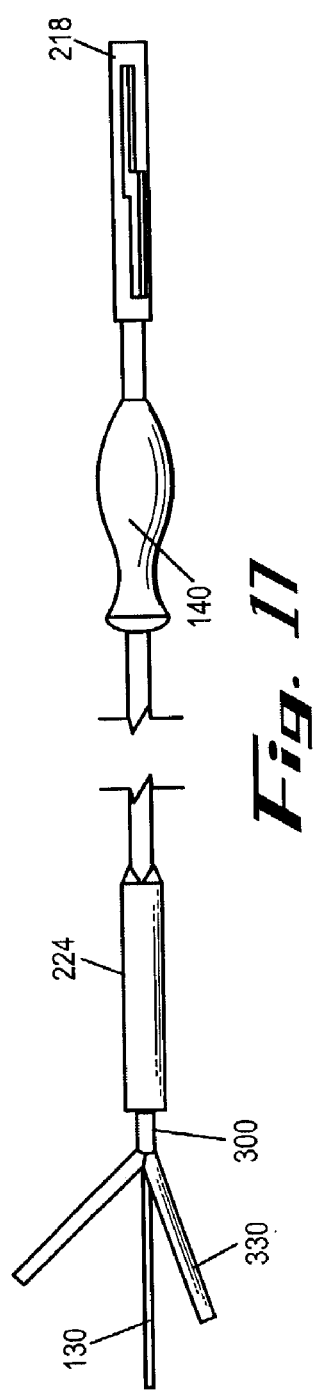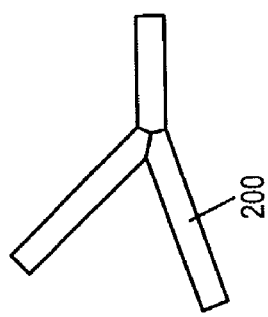

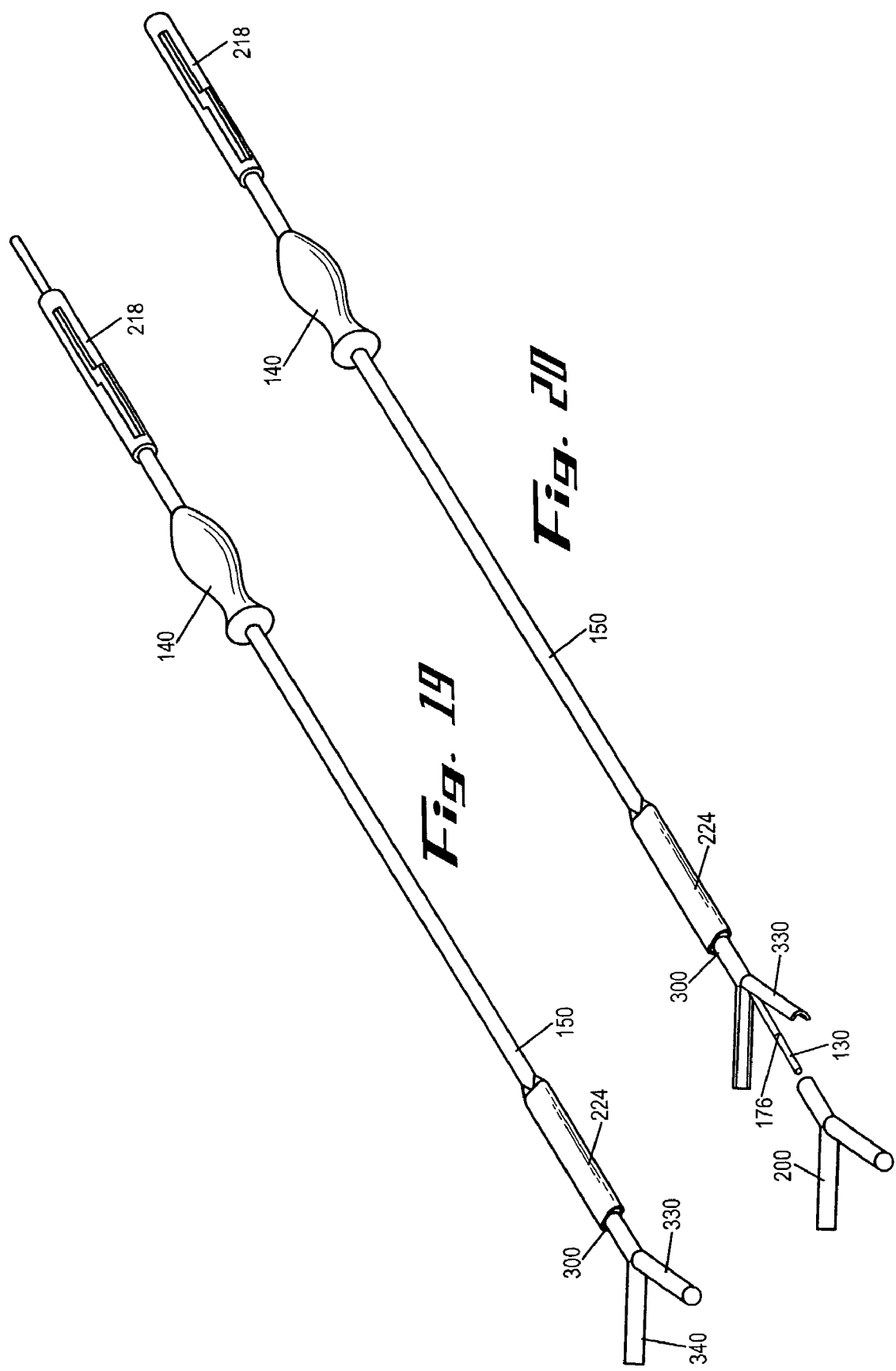

BIFURCATED MEDICAL APPLIANCE DELIVERY APPARATUS AND METHOD

FIELD OF THE INVENTION

The present invention relates generally to medical devices directed to the prevention of vascular and nonvascular vessel or passageway occlusion, and more particularly to stent deployment apparatuses and methods for utilizing these devices in the treatment of both benign and malignant conditions in bifurcated lumen.

BACKGROUND OF THE INVENTION

Over the last few years, physicians in interventional therapy in general and interventional cardiology and interventional radiology in particular have been attempting to find a way to deal with occluded (so called "stenotic") coronary arteries (among other blood vessels, various tubular conduits and similar structures) in a non-invasive manner while preventing restenosis. The issue is even more pronounced when dealing with bifurcated vessels. A blood vessel or similar conduit, which, along its course, extends a major branch vessel, is termed a "bifurcating vessel". The structural point of bifurcation, where the main trunk vessel and its side branch vessel meet, is termed the origin of the side branch, and the structure forming the angle between the vessels is termed the "carina".

Lesions that involve both the main trunk vessel and the side branch vessel are termed "bifurcating" lesions. Such lesions in a bifurcating epicardial coronary artery, involving a major side branch, are quite common. Typically, the side branch itself may contain significant atherosclerotic disease at, or in proximity to, its origin. Even in cases where the side branch is free of significant lesions, interventional manipulation of the main trunk vessel often results in compromising the side branch by a dissection, thrombus or spasm, or by causing a shift in the position of an atherosclerotic plaque in the main trunk vessel which partially or completely occludes the origin of the side branch. Accordingly, optimal management of bifurcating lesions involves treatment of both the main trunk vessel across the origin of the side branch as well as the origin and/or proximal segment of the side branch.

Attempts to treat such lesions have traditionally been by the serial installation of multiple stents or the simultaneous installation of modular stents (i.e. stents comprising a plurality of standardized units for use together in a cumulative group). In particular, attempts have been made to provide devices that allow the deployment of separate stents into each side branch. It would be preferable to provide an integrated stent that comfortably cradles the corina between the arms of the bifurcated stent as each arm of the bifurcated stent is delivered to a respective side branch. In particular, a bifurcated stents, such as the one disclosed in pending patent application Ser. No. 10/190,770, which is incorporated in its entirety by this reference, would be suitable for treatment of both vascular and nonvascular bifurcated vessels. Unfortunately, conventional delivery devices are not designed to effectively and accurately deliver such unitary bifurcated stents to their target site.

Therefore, there remains an existing need for apparatuses for accurate and minimally invasive placement and deployment of bifurcated stents. In particular, there is a need for a family of devices that may be indicated for vascular and non-vascular intervention. Moreover, there remains a need for a bifurcated stent placement and deployment apparatus that does not require the use of an ancillary means, such as one or more balloon catheters to achieve complete and precise deployment.

Additionally, there remains an existing need for a bifurcated stent delivery and deployment apparatus that has a safety mechanism to prevent excessive deployment of a misaligned stent. Preferably it would be desirable if the safety mechanism had a physical and/or audible indication means to inform the physician when she has reached maximum reversible deployment.

There also remains an existing need for a bifurcated stent delivery and deployment apparatus that increases physician control during stent deployment. Moreover, there exists a need for a bifurcated stent delivery and deployment apparatus that integrally comprises or allows for the insertion of an optical instrument to facilitate stent delivery.

There remains a need for a bifurcated stent delivery and deployment apparatus that also provides working channels for facilitating additional interventional procedures that may be necessary once the delivery and/or deployment process is underway.

SUMMARY OF EXEMPLARY EMBODIMENTS

It is a principal objective of an exemplary stent delivery and deployment apparatus in accordance with the present invention to provide a bifurcated stent delivery and deployment apparatus capable of accurately delivering a bifurcated stent to a target site. In the furtherance of this and other objectives, a delivery and deployment apparatus is provided that has an inner tubular member and an outer tubular member that are longitudinally and axially displaceable relative to one another. The device may alternatively have a middle tubular member that is also longitudinally and axially displaceable relative to the other tubular members. Moreover, in certain embodiments, the bifurcated stent is preferably housed within both a perforated biocompatible sheath and the outer tubular member such that the radial force exerted against the interior surface of the outer tubular member helps keep the bifurcated stent in place and avoids premature rupture of the biocompatible sheath.

Another objective of a preferred bifurcated stent delivery and deployment apparatus, in accordance with the present invention, is to provide a means for delivering unitary stents rather than modular stents to a target site.

Yet another objective, in accordance with the present invention, is to provide a bifurcated stent placement and deployment apparatus that does not require the use of an ancillary means, such as one or more balloon catheters to achieve complete and precise deployment.

It is an additional objective of a bifurcated stent delivery and deployment apparatus, in accordance with the present invention, to facilitate the precise delivery of bifurcated stents in a safe and repeatable fashion. In the furtherance of this and other objectives, a preferred deployment apparatus allows the physician to concentrate on correct placement without having to estimate extent of deployment. In particular, in a preferred embodiment, the present deployment apparatus has a physical safety mechanism that limits deployment to the critical deployment point (i.e., ~60%). The critical deployment point may range form 5% to 95% but is preferably about 60%. At this point, if the physician is satisfied with placement, she can engage the safety means to what we refer to as the Proceed Orientation (PO) and fully deploy the stent. It is preferred that when the safety mechanism is engaged to the PO, a physical twist and a possible audible indicator sounds to inform the physician that if she deploys the stent any further, she can no longer retract the stent beyond this point. Though the present stent and delivery system eliminates the need for repositioning, such safety features are still preferable. In a preferred embodiment, the slight audible indication is the sound of a tab or stop snapping to allow free deployment of the stent.

An additional objective of a preferred embodiment of the present invention is to provide a stent delivery and deployment apparatus where the handle portion is held and the outer tubular member of the device is retracted.

An additional objective in accordance with an exemplary embodiment of the present invention is to provide a stent deployment apparatus that allows for the insertion of an optical instrument to facilitate stent delivery. In the furtherance of this and other objectives, it is envisioned that an ultra thin optical scope or optical guidewire may pass through a channel in preferably the middle tubular member, but may also pass through the interior diameter of the inner tubular member or portion of the outer tubular member or both. The device is also capable of letting a flexible optical scope of about 5-6 mm diameter be coupled along the exterior of the outer tubular member thereof. Alternatively, it is envisioned that an ultra thin optical scope may pass along side the guidewire through the internal diameter of the inner tubular member of the device. In accordance with this embodiment, the guidewire itself may be the scope.

An additional objective in accordance with an alternative embodiment of the present invention is to provide a stent delivery and deployment apparatus that has a middle tubular member and/or outer tubular member of sufficient cross sectional thickness to define at least one longitudinally extending channel for receiving additional utility tools. In the furtherance of this and other objectives, and by way of example only, one such channel could accommodate an ultra thin scope while an alternative channel receives a guidewire, syringe systems, etc. Principally, these channels are suitable for receiving a number of other tools that a physician may need during deployment of a stent or therapeutic treatment of target tissue.

Still another objective in accordance with a preferred embodiment of the present invention is to provide a device having direct visualization capabilities directly incorporated into the device. In one design of such embodiment, the inner, middle or outer tubular members individually or collectively serve as an optical device. Moreover, in embodiments where the middle or outer tubular members have utility channels, the channels may themselves be comprised in whole or in part of optically active materials. In the furtherance of this and other objectives, at least one of the inner, middle or outer tubular members comprises at least one optical fiber coupled to a lens and light source to provide direct visualization during deployment. In such embodiments, which provide direct visualization, the safety mechanism is not required to assure accurate delivery and deployment.

In addition to the above objectives, an exemplary stent deployment apparatus preferably has one or more of the following characteristics: (1) applicable for various interventional applications such as addressing stenosis; (2) biocompatible; (3) compliant with radially expanding stents; (4) capable of distal or proximal stent release; (5) smooth and clean outer surface; (6) length of the device variable according to the insertion procedure to be employed; (7) outer dimension as small as possible (depends on the diameter of crimped stent); (8) dimensions of the device must offer enough space for the crimped stent; (9) radiopaque markers, preferably on the inner tubular member, to indicate proximal and distal ends of the stent; (10) sufficient flexibility to adapt to luminal curvatures without loss of ability to push or pull; (11) low friction between the inner tubular member and outer tubular member; (12) sufficient resistance to kinking; (13) good deployment, ability to reposition partially deployed stent; (14) added with a scale to observe the stent position during the insertion procedure; (15) insertion procedure should require low force; or (16) sufficiently economical to manufacture so as to make the deployment apparatus disposable.

Further objectives, features and advantages of the invention will be apparent from the following detailed description taken in conjunction with the accompanying drawings.

BRIEF DESCRIPTION OF THE FIGURES

FIG. 3 is a perspective view of the delivery and deployment apparatus of FIG. 2, where the outer tubular member has been partially retracted to allow the delivery of each arm of the bifurcated stent to its respective branch and where the biocompatible sheath begins to split along the predetermined perforation line;

FIG. 4 shows a perspective view of further deployment of the bifurcated stent of FIG. 1 wherein the biocompatible sheath has disassociated from the bifurcated stent;

FIG. 5 is a perspective view of the bifurcated stent of FIG. 1 encased in the biocompatible sheath, wherein the predetermined perforation line is shown;

FIG. 13 is a front perspective view of the distal region of an exemplary embodiment of a delivery and deployment apparatus in accordance with the present invention showing the perforated middle tubular member;

FIG. 14 is an elevational view of the distal region of the delivery and deployment apparatus of FIG. 13;

FIG. 15 is a side view of sections of the delivery and deployment apparatus of FIG. 18;

FIG. 16 is a side view of sections of the delivery and deployment apparatus of FIG. 18 showing the exposed middle tubular member having a bifurcated stent retainer extended from the outer tubular member;

FIG. 17 is a side view of sections of the delivery and deployment apparatus of FIG. 18 showing the exposed middle tubular member having a bifurcated stent retainer extended from the outer tubular member and a stent deployed distal thereto.

FIG. 18 is a perspective view of a delivery and deployment apparatus in accordance with the present invention;

FIG. 19 is a perspective view of a delivery and deployment apparatus in accordance with the present invention showing the exposed middle tubular member having a bifurcated stent retainer extended from the outer tubular member;

FIG. 20 is a perspective view of a delivery and deployment apparatus in accordance with the present invention showing the exposed middle tubular member having a bifurcated stent retainer extended from the outer tubular member and a stent deployed distal thereto;

DETAILED DESCRIPTION OF AN EMBODIMENT

Figure 2:
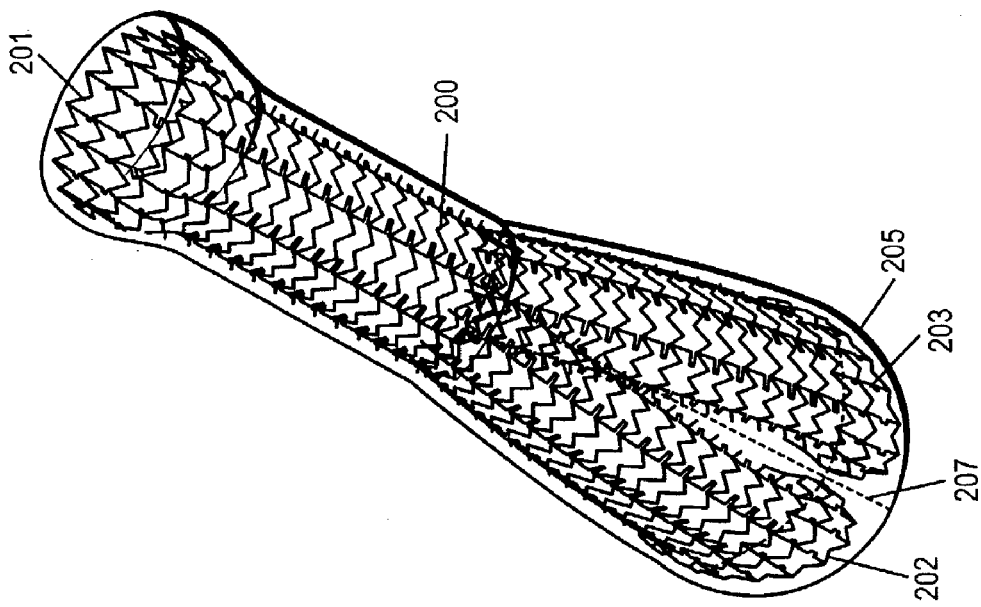
FIG. 2 is a perspective view of a delivery and deployment device in accordance with the present invention, showing the stent encased within the biocompatible sheath inside the outer tubular member and resting distally at the corina of a target tissue.
Figure 1:
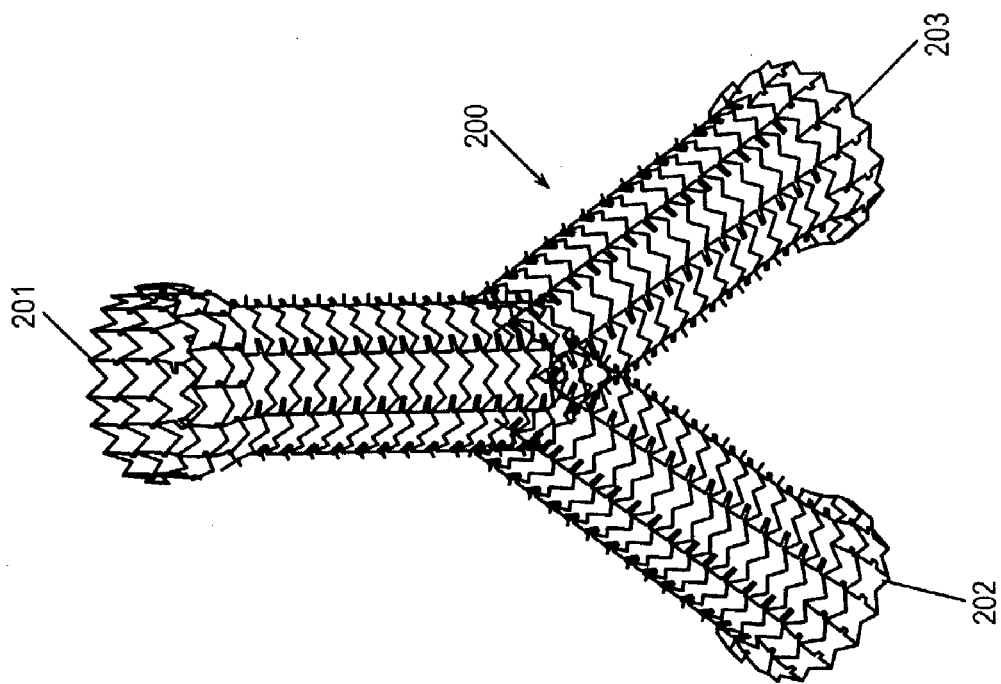
FIG. 1 is a perspective view of an exemplary bifurcated stent to be delivered and/or deployed by an apparatus in accordance with the present invention.
Figure 6:
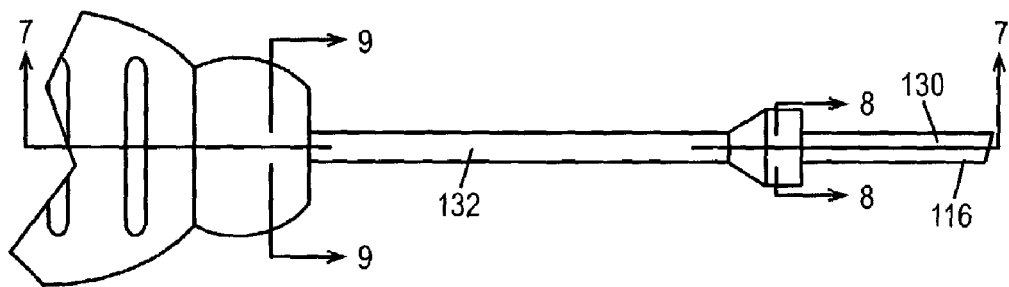
FIG. 6 depicts enlarged views of portions of the deployment safety mechanism.
Figure 7:
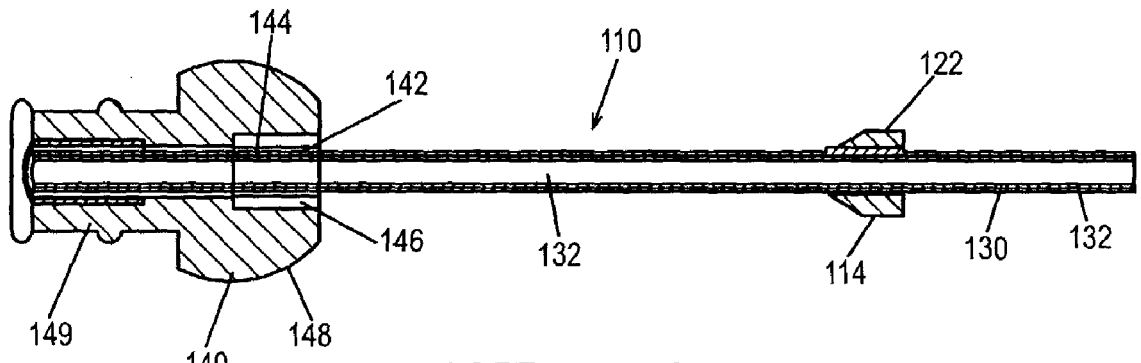
FIG. 7 shows a cross section view of the deployment safety mechanism along lines 7-7 of FIG. 6.
Figures 8, 9:
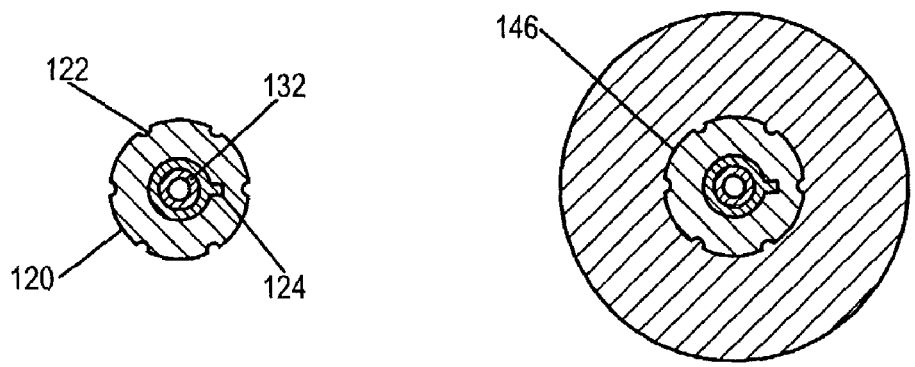
FIG. 8 is a perspective view of a portion of the complementary portion of the deployment safety mechanism region of the handle as shown along lines 8-8 of FIG. 6.
FIG. 9 is a perspective view of the stop of the deployment safety mechanism as shown along lines 9-9 of the device of FIG. 6.

A preferred embodiment of the present deployment apparatus comprises inner and outer tubular members (i.e., the tubular members are preferably nonpyrogenic), interactively coupled with each other in a manner that one can move rotationally and proximally or distally with respect to the other. The inner tubular member and the outer tubular member can be displaced relative to each other in longitudinal direction as well as in a radial direction. The deployment apparatus in accordance with the present invention can be used most advantageously for the placement of unitary bifurcated stents. A stent suitable for such procedures would be one in accordance with the disclosures, in co-pending U.S. patent application Ser. No. 10/190,770 and International Application Serial No. PCT/DE02/01244 incorporated herein in their entirety by this reference. These stents have a small radial diameter at a low temperature, while they expand radially when exceeding an upper threshold temperature, so that they can keep a stenosis open in this manner. It is particularly advantageous to use stents of an alloy of nickel and titanium, the so-called nitinol. Alternative embodiments of these stents provide an aperture about the apex of the stent (which will rest about the corina of the bifurcated lumen) to facilitate direct visualization there through.

In relevant embodiments, when the stent is inserted and after the corina has been reached, the outer tubular member is retracted, so that the stent is released. Alternatively, the distal end of the outer tubular member may be placed short of the corina so that the inner tubular member may be extended so that the stent is placed in direct contact with the desired location prior for expansion. A self-expanding stent then by itself assumes the expanded position. This eliminates the need for post expansion positioning techniques. With an alternative embodiment of the device, the device has fasteners that retain contact with a portion of the stent in the event that the stent needs to be retracted or repositioned.

In order to deliver the stent, the deployment apparatus in accordance with the present invention is capable of accurately delivering a bifurcated stent to a target site by allowing the bifurcated stent to be housed within both a perforated biocompatible sheath and the outer tubular member such that the radial force exerted against the interior surface of the outer tubular member helps keep the bifurcated stent in place and avoids premature rupture of the biocompatible sheath.

The total length of the deployment apparatus varies based on the location of the target lumen. However, these dimensions may differ as a function of the stent diameter and/or if an optical scope integrally provided to facilitate stent delivery. The outer tubular member may be configured to allow for the coupling of an optical stent along the Exterior Diameter thereof. Alternatively, the Interior Diameter of the inner tubular member may be enlarged sufficiently to accommodate the optical scope and additionally the increased crimped stent diameter. However, it is expected, though not required, that the smallest diameter that allows for example a nanofiber scope to pass, will be employed in this alternative embodiment. It should be understood that through hindsight, after exposure to the present specification, one of ordinary skill would be able to adapt the current device to receive an ultra thin optical scope to the internal diameter of the device without undo experimentation and without departing from the spirit of the present objectives.

In an alternative embodiment, an integrated direct visualization system is provided wherein an optical cable is coupled with a portion of or comprises the hypotube and preferably capable of extending beyond both the distal and proximal ends of the deployment device such that viewing of any segment of the lumen is possible. In such embodiments, the camera and light source are preferably operatively coupled and disposed about the distal region of the apparatus. An exemplary deployment apparatus in accordance with the present invention is durable while affording adequate flexibility to navigate through anatomical lumens without kinking. To this end, it is preferable that the deployment apparatus is formed of biocompatible synthetics and in a preferred embodiment reinforced with metal structure. This allows for deployment within an accuracy of about ±3 mm.

The following reference numbers and corresponding stent placement and deployment device components are used when describing the device in relation to the figures:

| | |
|---|---|
| 100 | Delivery & Deployment Device |
| 112 | Guidewire |
| 114 | Proximal Handpiece |
| 116 | Hypotube |
| 118 | Safety Mechanism |
| 120 | Stop |
| 122 | Stop Female Locking Member |
| 124 | Tab of the Stop |
| 130 | Inner Tubular Member |
| 132 | Inner Tubular Member Interior |
| 134 | Inner Tubular Member Exterior |
| 136 | Proximal End of Inner Tubular Member |
| 138 | Inner Tubular Member Distal End |
| 140 | Handle |
| 142 | Handle Proximal Cavity |
| 143 | Inner Channel of Handle |
| 144 | Base of Handle Cavity |
| 146 | Male Locking Member |
| 148 | Inner Handle Hub |
| 149 | Outer Handle Hub |
| 150 | Outer Tubular Member |
| 152 | Outer Tubular Member Exterior |
| 154 | Outer Tubular Member Distal Region |
| 156 | Outer Tubular Member Interior |
| 158 | Exterior Tubular Member |
| 176 | Pusher |
| 180 | Proximal Marker |
| 182 | Medial Marker |
| 184 | Distal Marker |
| 190 | Hypotube Detent |
| 200 | Stent |

-continued

| 201 | Stent Primary Lumen |
| 202 | Stent Right Branch Lumen |
| 203 | Stent Left Branch Lumen |
| 205 | Biocompatible Sheath |
| 207 | Sheath Perforation |
| 210 | Channel Safety Mechanism |
| 215 | Corina |
| 218 | Safety Mechanism |
| 224 | Device Distal Region |
| 242 | Safety Track |
| 244 | Safety Catch |
| 300 | Middle Tubular Member |
| 330 | Bifurcated Stent Retainer |
| 340 | Stent Retainer Seam |
| 350 | Utility Channel |

It should also be pointed out at the outset that various embodiments of stent delivery and deployment devices in accordance with the present invention make reference to guidewires and/or optical instruments. In some embodiments the terms may overlap since it is contemplated within the scope of such embodiments that the guidewire itself has visualization capabilities resulting from the guidewire being an ultra thin optical and/or ultrasound device. It should also be evident from the following disclosure that independent placement of traditional and visualization capable guidewires as well as guidewires integrally coupled with the device for placement and deployment of a stent is contemplated and should be considered as residing within the scope of the claims.

By way of general discussion, and not referring to any specific figure, the present invention, in preferred embodiments provide placement and deployment devices that include an outer tubular member and an inner tubular member, wherein the outer tubular member and the inner tubular member can be displaced relative to each other. At the proximal end of an exemplary device is a threaded female luer, coupled with a portion of the inner tubular member and preferably a portion of a hypotube. As stated earlier, a suitable alternative terminus may be employed as long as it provides the minimum benefits provided by a luer. The hypotube is disposed about the inner tube and extends from a location adjacent to the luer through a portion of the handle of the deployment apparatus. In an alternative embodiment, the hypotube terminates within the luer. A safety mechanism is provided that is formed in part by the complementary fitting of a portion of the handle and a stop coupled with the hypotube between the luer and the handle. The stop is preferably molded onto the hypotube, the molding process resulting in a tab formed on the stop that is subsequently broken when the physician desires to place the deployment apparatus in the proceed orientation. In an exemplary embodiment, when the tab is broken and the deployment apparatus is placed in the proceed orientation; the stop may potentially rotate freely about the hypotube. It should be kept in mind that the stop may take a variety of shapes, including but not limited to, rectangular, round, conical etc. In a preferred embodiment, the stop is conical with a tapered effect to facilitate entrance and removal from the base handle cavity.

As illustrated in FIGS. 6-9, a preferred stop 120 includes female locking members 122 comprising channels formed along the exterior thereof that are complementary to the male locking members 146 formed on the interior cavity 142 along the proximal region of the handle 140. The male locking members 142 and female locking members 122 can be formed into any shape or suitable size as long as they do not depart from the essential purpose of forming safety mechanism. The cavity 142 of the handle 140 is designed to receive the stop 120 and prevent further deployment. As a result, the stop 120 is molded at a distance along the hypotube 116 such that the distance between the distal end of the stop 120 and the base 144 of the complementary cavity 142 of the handle 140 roughly corresponds to the critical deployment point. It should be noted that the female locking members 122 and male locking members 146 of the safety mechanism 118 might be reversed so that the female locking members 122 and male locking members 146 are on the handle 140 and the stop 120, respectively. Additionally, alternative safety mechanisms, varying in size, shape and manner, may be employed to ensure accurate deployment beyond the critical deployment point.

The handle 140 is preferably molded to a portion of the outer tubular member 150, which extends from the handle 140 to the distal tip 160 of the device 110. The outer tubular member 50 is disposed about the inner tubular member 130. In an exemplary embodiment, the outer tubular member 150 is clear so that the inner tubular member 150 is visible there through. Moreover, markers (not shown) preferably formed on portions of the outer tubular member 150 are also visible.

Referring now to FIGS. 2-4, in the distal region of the inner tubular member 130, a portion of the biocompatible sheath 205 is coupled thereto. Moreover, the stent 200 is preferably adjacent the distal end 138 of tubular member 138. Though not necessary, there may be other means (not shown) of releasably holding the stent during the placement procedure, such as adhesives, clamps, suture, etc. In a preferred embodiment, the biocompatible sheath 205, at the proximal end of the stent 200 is open so as to accommodate the distal end 138 of inner tubular member 130 as well as allow the passage of an optical instrument into the primary lumen 201 of the stent 200 or even one of the stent branch lumens 202 and 203. When the stent 200 is adjacent the distal end 138 of the inner tubular member 130 and a portion of the biocompatible sheath 205 is coupled with the inner tubular member 130, the stent is sufficiently secure to remain in place during the delivery procedure.

In order to prevent the stent 200 from prematurely deploying, the sheathed stent 200, during the delivery procedure, is housed within the internal diameter 156 of the outer tubular member 150. The outward radial force exerted by the stent 200 against the interior surface 156 of the outer tubular member 150 is sufficient to prevent premature deployment while not sufficient hinder the requisite flexibility of delivery and deployment device 110.

In practice, the physician can retract the outer tubular member 150 with respect to the inner tubular member 130, which exposes the right 202 and left 203 branch lumens of the stent 200. Moreover, the outward radial force is no longer against the interior surface 156 of the outer tubular member 150, which allows for more extensive expansion of the stent 200. As the stent incrementally expands, the outward force begins to rupture the perforation 207 of the biocompatible sheath 205 and further allowing the stent 200 to disassociate with the distal end 138 of the inner tubular member 130 and deploy to the target site.

During the procedure, the delivery and deployment apparatus 110 is preferably installed such that the distal end of the stent 200 rests about the corina 215 so that when the stent 200 is deployed, stent branch lumens 202 and 203 are delivered to their respective branches.

The device is configured such that an optional guidewire 112 may be passed through the internal diameter 132 of the inner tubular member 130 through the proximal handpiece 114 at the proximal end, the primary lumen 201 of the stent 200 at the distal end and the inner tubular member 130 there between. In an alternative embodiment, the internal diameter 132 of the device 110 is sufficient to receive an optical scope there through. In this alternative embodiment, the optical scope may pass about the guidewire 112 from the proximal to and through the distal ends of the delivery and deployment apparatus 110. This is so as to allow the physician to view a patient's anatomy that may lie distal of the distal stent 200. In an additional embodiment, a single fiberscope may be provided that is coupled with the guidewire 112. As stated before, the optical instrument itself may be an ultra thin guidewire with optical and/or ultrasound capabilities.

Additionally, the outer tubular member 150 and the inner tubular member 130 may be adapted so that instead of feeding the optical scope through the proximal handpiece 114, the mating apertures are formed on along a portion of the longitudinal expanse of the inner tubular member 130 and an entry point formed on a portion of the outer tubular member so as to receive the scope through both the inner tubular member 130 and the outer tubular member 150 even as the inner tubular member 310 and outer tubular member 150 are moved rotationally and proximally or distally with respect to the other.

Referring to the functional aspects of the device 110, present invention provides a delivery and deployment apparatus 110 that includes an elongate and flexible outer tubular member 150 constructed of at least one biocompatible thermoplastic elastomer, e.g. such as polyurethane and nylon. A central lumen 156 runs the length of the outer tubular member 150. A distal region 154 of the outer tubular member 150 surrounds the stent 200 to be placed, and maintains the stent in a crimped delivery configuration, against an elastic restoring force of the stent 200. The stent 200, when in a normal unrestrained configuration, generally has a diameter substantially larger than the interior diameter 132 of the inner tubular member 130. Typically the expanded stent 200 is larger in diameter than the body lumen in which the stent is fixed, and the restoring force tends to maintain the stent against the tissue wall.

Outer tubular member 150 is mounted at its proximal end to a handle 140. Outer tubular member 150 can be pushed and pulled relative to inner tubular member 130 by hand manipulation of the handle 140 at the proximal end of the outer tubular member 130 and holding the proximal end of the handle 140.

In a preferred embodiment, there are also markers (not shown) coupled with portions of the outer tubular member 150. The markers are constructed of a radiopaque material, e.g. platinum iridium, and preferably surround the outer tubular member 150. Markers are axially spaced apart to mark the length of the stent 200 and to mark the critical deployment distance for that stent length. Markers 80 and 84 have Exterior Diameters slightly smaller than the interior diameter of outer tubular member 50. The outer tubular member 50 thus functions in part as a measuring and retaining means for radially compressing the stent and maintaining the stent 200, so long as the outer tubular member 150 surrounds the stent 200. It should be noted that the markers may be more or fewer in number and may also be formed about the interior diameter 32 of the inner tubular member 30 or alternatively, about the interior diameter 56 or exterior diameter 58 of the outer tubular member 50.

A guidewire 112 is preferably disposed within the interior lumen 132 of an elongate and flexible inner tubular member 130, which can be constructed of materials similar to those employed to form the outer tubular member 150. However, it is preferable that inner tubular member 130 is formed from a more durable material and additionally no guidewire may be necessary. A biocompatible sheath 205 containing the stent 200 is operably coupled with a portion of the inner tubular member 130 about the distal end thereof.

Inner tubular member 130, along its entire length, has an interior lumen 132 open to both the proximal and distal ends of the inner tubular member 130. In certain direct visualization embodiments, the modified bifurcated stent (not shown) is provided so that the preferred optical instrument can pass through the inner tubular member 130 and through the primary lumen 201 and apex of the stent 200 for visualization at and distal the apex of the bifurcated stent 200.

Handle 140 and outer tubular member 150 are movable relative to inner tubular member 130. More particularly, the handle 140 is moved proximally relative to the inner tubular member 130, facilitating the movement of outer tubular member 150 relative to inner tubular member 130 so as to provide a means for controllably withdrawing the outer tubular member 150, relative to the inner tubular member 130, resulting in the release of the stent 200 for radial self-expansion.

The following is a discussion of a preferred embodiment of the device 110 in use but in no way should be construed as limiting with respect to structure and/or method of use.

When the device 110 is used to position the stent 200, the initial step is to position guidewire 112 within the anatomy of a patient. This can be accomplished with a guide cannula (not illustrated), leaving guidewire 112 in place, with the exchange portion of the guidewire extended proximally beyond the point of entry into the anatomy of the patient. Deployment apparatus 110 is then advanced over the guidewire 112 at the exchange portion, with the guidewire 112 being received into the inner tubular member 130. As device 110 is inserted into the body, the proximal portion of guidewire 112 travels proximally (relative to the device) to the proximal end of guidewire lumen 132.

Once device 110 is positioned, the physician maintains guidewire 112 and inner tubular member 130 substantially fixed with one hand, while moving handle 140 in the proximal direction with the other hand, thus to move outer tubular member 150 proximally relative to inner tubular member 130. As the outer tubular member 150 is retracted, the stent 200 remains substantially fixed relative to inner tubular member 130, and thus radially self-expands. As the handle 140 and correspondingly the outer tubular member 150 are retracted, the handle 140 encounters the safety mechanism 118 for the critical deployment point. The inner tubular member 130, via the handle 140, may have to be rotated to align and insert the stop 120 into the handle 140. When fully inserted, further deployment cannot occur without twisting and snapping the stop the tab 124 portion of the stop 120. Continued retraction of the outer tubular member 150 results in complete deployment of the stent.

After deployment, the stent ideally radially self-expands to a diameter greater than the diameter of outer tubular member 150. Guidewire 112 can be withdrawn as well. The guidewire 112 emerges from the proximal end of the proximal handpiece 114. However, should the medical procedure involve further treatment, e.g., placement of a further stent, the deployment apparatus 110 can be removed without removing the guidewire 112. Device 110 is removed by progressively pulling the device away from the guidewire 112 (which removes the guidewire from within the inner tubular member 130), all while maintaining guidewire 112 in place.

With respect to additional safety features incorporated in the present device 110, in a preferred embodiment, the device 110 has a deployment safety mechanism 118 that comprises male 146 and female 122 locking members that are brought into functional engagement as the stent is being deployed.

Once the stent has reached the critical deployment point, the distal end of the stop 120 is substantially flush with the base 144 of the handle cavity 142 and the female locking members 122 of the stop 120 are in operative communication with the corresponding male locking members 146 formed on the interior surface of the cavity 142 of the handle. When the safety mechanism 118 is engaged as described above, the stent cannot be deployed further without physician intervention. In order to deploy the stent beyond this point, the physician has to rotate the stop 120 to cause the tab 124 to break. Once the tab 124 is broken, the device 110 is in the proceed orientation and deployment may proceed.

In a preferred embodiment, the physician will feel a tactile indication that the device 110 can be deployed further. Alternatively, the breaking of the tab may also, or as a substitute to tactile indication, results in an audible indication that further deployment is possible. Additionally, the physician is apprised of the fact that deployment beyond this point is irreversible except for interventional retrieval methods. As discussed earlier, the critical deployment point is preferably about 60% deployment, beyond which retraction is not recommended. As a result, the safety mechanism 18 removes the need to estimate extent of deployment and provides a reliable means of accurately deploying stents. Alternative locking mechanisms may be provided as long as they retain the important characteristic of giving the physician a sensory indication of extent of stent deployment and removes the need to estimate extent of deployment. By way of non-limiting example only, the locking mechanism could comprise a breakable seal, tab/stop lock, diverted channel safety mechanism, etc.

Figure 10:
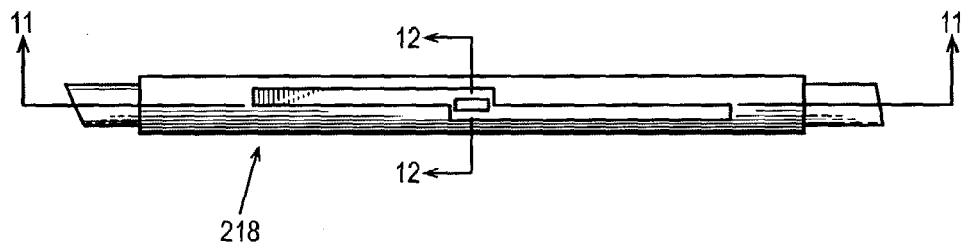
FIG. 10 is a perspective view of a portion of a deployment safety mechanism in accordance with the present invention.
Figure 11:
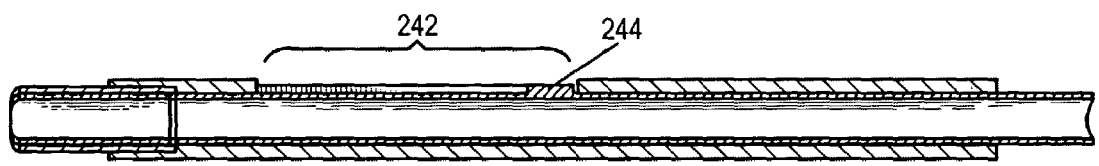
FIG. 11 is a perspective view of the slide cavity of the safety mechanism as shown along lines 11-11 of the device of FIG. 10.
Figure 12:
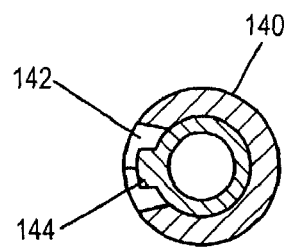
FIG. 12 is a perspective view of a portion of a deployment safety mechanism as shown along lines 12-12 of FIG. 10.
Figure 1B:
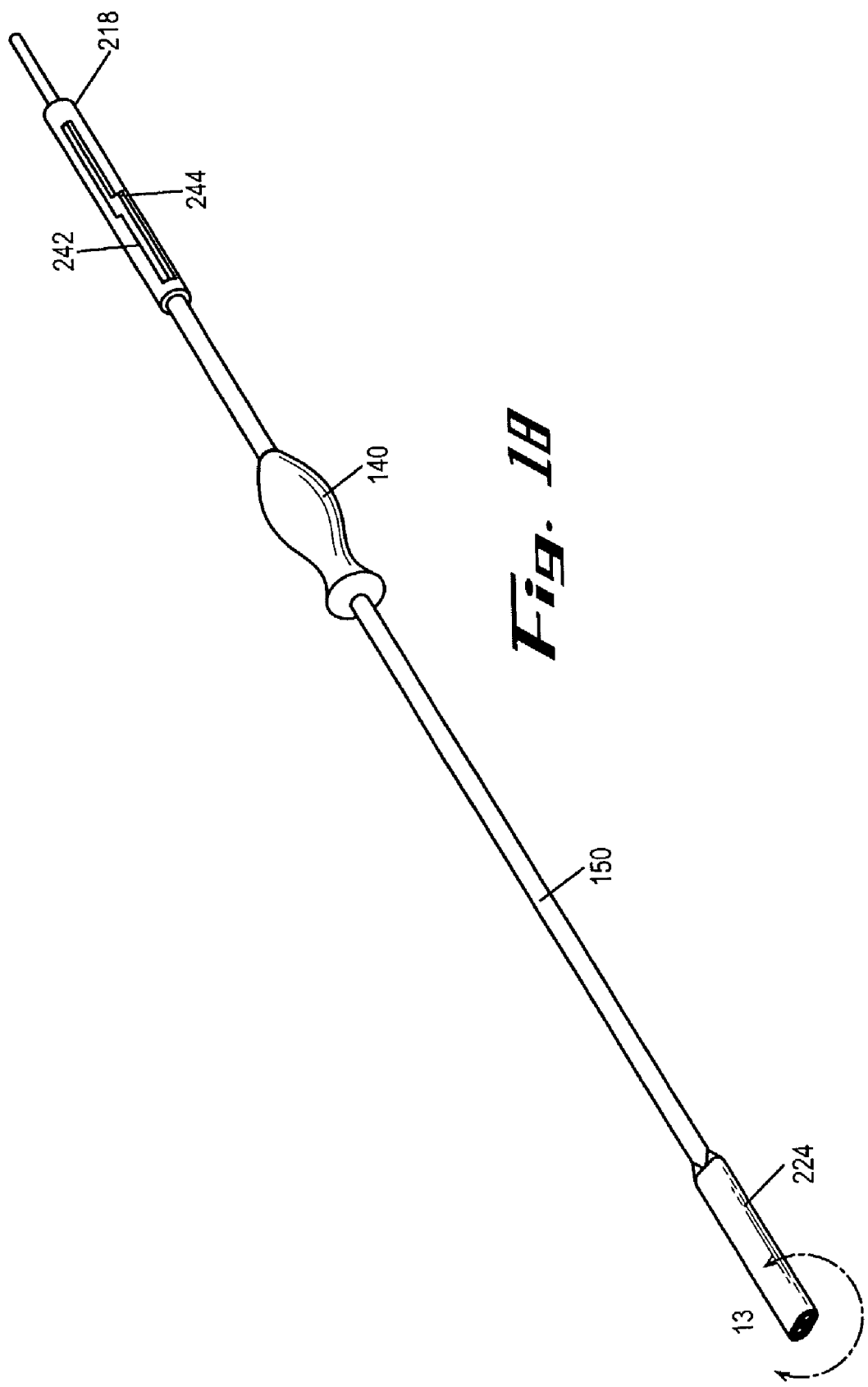
Figure 21:
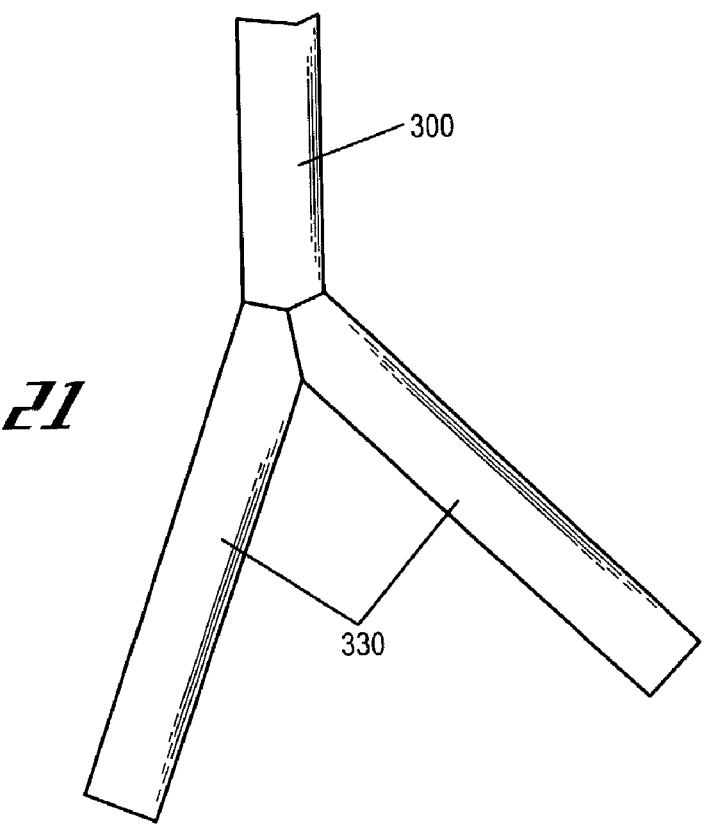
FIG. 21 is a perspective view of the distal region of the middle tubular member showing an embodiment with an anatomically correct shape of the bifurcated stent retainer for use in a human trachea.
Figure 22:
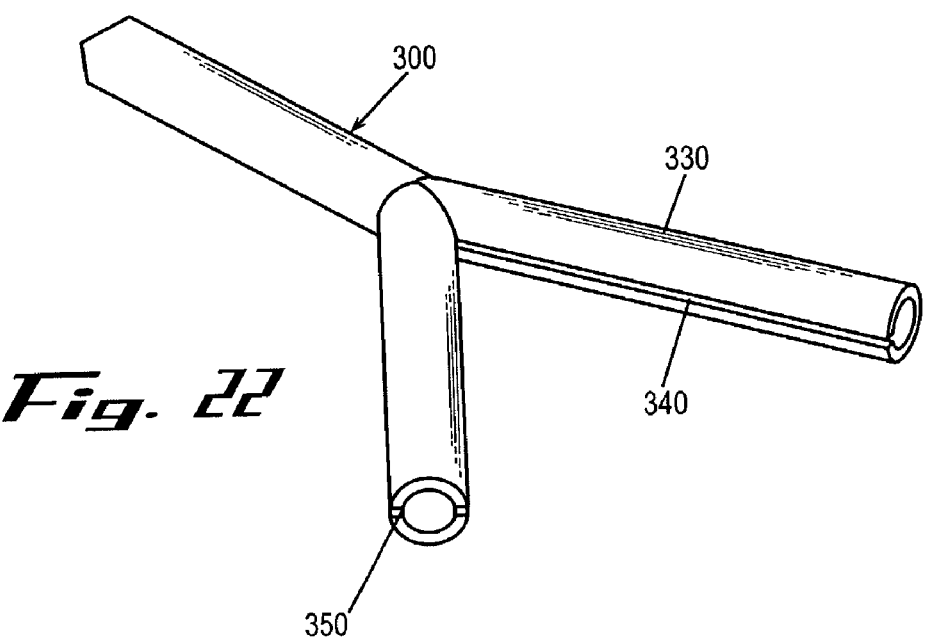
FIG. 22 is an isometric view of the distal region of the middle tubular member, which terminates with a bifurcated stent retainer with interior seams for releasably deploying the stent.

Referring specifically to FIG. 10, a diverted channel safety mechanism is provided generally as 118. In particular, about the stop 120 or as an alternative to the stop 120, a detent 190 is coupled with the hypotube 116. As the hypotube 116 and inner tubular member 130 are advanced distally or, alternatively, the outer tubular member 150 is retracted proximally, the detent 190 comes into contact with the base 144 of the cavity 142 of the handle 140. The handle 140, in this alternative embodiment, defines a substantially Z shaped channel 143 that is essentially a continuation of the cavity 43. The shape of the channel 143 may vary from an L, S, T or other suitable shape for encouraging user intervention. In practice, physician intervention comprises the step of rotating the hypotube 116 such that the detent 190 no longer abuts the base 144 of the handle cavity 142, rather once rotated, the detent 190 is disposed within the channel 43 of the handle 40 allowing free stent deployment. In the furtherance of this safety mechanism 118, it is preferable that the point of detent/base interaction is about approximately the critical deployment point. The principal thrust of this and other safety mechanisms that fall within the scope of this invention is that deployment is limited to a point where the stent and the device are still retractable absent additional user intervention. Beyond this point, the user understands that deployment may not be easily aborted and reversed. The principal feature is the requirement of user intervention in order to fully deploy the stent. This insures that stents are not prematurely deployed. It should also be kept in mind that all of the alternative embodiment of the present invention may be provided with varying dimensions depending on the interventional necessity. For example, as discussed above, the device 10 may have longer or shorter overall dimensions depending on the deployment protocol.

In an alternative embodiment of a Y stent delivery and deployment apparatus, as shown generally in FIGS. 13-22, an alternative delivery mechanism is provided in the distal region 224. In particular, a middle tubular member 300 is provided, which terminates at its distal end with a bifurcated stent retainer 330. The bifurcated stent retainer 330, as more specifically shown in FIGS. 21-22, allows the right 202 and left 203 branch lumens of stent 200 to disassociate from one another sufficiently to allow their distal ends to satisfactorily cradle the corina of the target branched tissue when the outer tubular member 150 is retracted. Additionally, the bifurcated stent retainer 330 exerts sufficient compression force against the stent 200 to prevent it from prematurely expanding. Taking specific note of FIG. 21, in embodiments where the target tissue is the human trachea, the middle tubular member 300 terminates with the bifurcated stent retainer 330 which has a general configuration that is anatomically correct with respect to the human trachea in that the legs that hold the right 202 and left 203 branch lumens of the stent 200 are offset at asymmetric angles. This allows for more accurate placement and deployment of the stent 200.

In a preferred embodiment, the bifurcated stent retainer 330 has an interior seam 340 that can be ruptured with sufficient force to allow the stent 200 to move distally there from and radially expand to its expansion diameter. It should be pointed out that the seam may be located anywhere along the circumference of the bifurcated stent retainer 330 and in alternative embodiments, no seam is necessary. The key principal is to have a retainer 330 that can keep the stent 200 from deploying when the outer tubular member 150 is retracted, while allowing for the egress of the stent 200 from the retainer 330 when the stent 200 has been properly aligned for deployment.

Referring specifically to FIGS. 18-20, in accordance with a preferred embodiment, the present delivery and deployment apparatus 100 provides a pusher 176 formed on a portion of the inner tubular member 130. Preferably, the pusher 176 rests about the proximal end of the primary lumen 201 of the stent 200. The pusher allows the physician, when the inner tubular member 130 is extended distally with respect to the outer 150 and/or middle 300 tubular members, to disassociate the stent 200 from the bifurcated stent retainer 330 by urging the stent 200 distally. In the embodiments comprising a seam 340, proximally oriented force causes the seam 340 to rupture and allows for egress of the stent 200 from the bifurcated stent retainer 330. Alternatively, the middle tubular member 300 may be retracted proximally with respect to the inner tubular member 130, resulting in stent egress. It is also possible to manipulate the inner 130 and middle 300 tubular members simultaneously.

It should be kept in mind that though these alternative embodiments contain a middle tubular member 300, the safety mechanism principally works the same with regard to the critical deployment point. Essentially, the critical deployment point is more critically tied to the relationship between the inner 130 and the middle 300 tubular members rather than the inner 130 and outer 150 tubular members in the earlier embodiments. In the embodiments having a middle tubular member 300, retraction of the outer tubular member does not have to result in irreversible deployment. However, when the inner tubular member 130 and the middle tubular member 300 are moved proximally or distally with respect to each other, too much movement may result in full deployment. In such instances, the safety mechanism will limit proximal and/or distal dislocation to a predetermined length that cannot be exceeded without user intervention.

Referring again to the desirability to have the ability to provide additional utility instruments for further interventional treatment, devices in accordance with a preferred embodiment of the present invention comprise utility channels 350 that are preferably defined by middle tubular member 300 but may also be provided through outer tubular member 150. Furthermore, interior 132 of inner tubular member 130 may serve the same function as utility channel 350 in middle tubular member 300. As shown in the figures, utility channel 350 may be an extension of the interior of middle tubular member 300, or alternatively, the utility channels may run the outer surface of middle tubular member 300 (not shown).

An example of a suitable instrument passed along the utility channels 350 of the bifurcated stent retainer 330 and the utility would be a guidewire 112, though many other useful instruments may be employed, limited only by the need to keep the exterior diameter of the bifurcated stent retainer 330 within a range that can fit in the lumen in which the device 100 will be introduced. Moreover, the guidewire could be a standard guidewire, or alternatively a specialized ultra thin guidewire having optical capabilities.

An alternative instrument is a syringe system (not shown) that can be integrally coupled with the delivery and deployment device 100 or alternatively configured to pass through either the utility channel 350 of the middle 300 tubular member or suitable portions of inner 130 or outer 150 tubular members, respectively. An exemplary syringe system may have thermotherapy, cryotherapy, photodynamic, chemotherapy capabilities or combinations of these capabilities. In either configuration, but particularly the chemotherapeutic embodiment, the syringe system provides an extendable/retractable needle for delivering a therapeutic dose of a bioactive product such as a chemotherapeutic agent. It should be noted that the needle may alternatively be, for example, an electrocautery probe, for certain thermotherapy indications, or the bioactive product may be a suitable photosensitizer, in certain photodynamic therapy indications. Therefore, in order to adapt to the desired capabilities and a variety of indications, the general syringe system may be adapted in accordance with methods known in the art without requiring undue experimentation. It is preferable, in the chemotherapeutic and/or the photodynamic application, however, that the needle be introduced into a target lesion and the bioactive product introduced. It should be noted that the syringe system is useful in both malignant and benign applications. In a preferred embodiment, the syringe system comprises a needle at the distal end and a reservoir of bioactive product proximally situated, with a conduit servicing the needle and reservoir there between. The syringe system is configured to provide for extension and/or retraction of the needle to a target site in both the stand alone and integrated configurations. The stand-alone version is a general reference to the embodiment that is suitable for situating through appropriate channels of the device, but is not coupled thereto.

The various utility instruments referenced above, may take the form of a number of devices but, by way of non-limiting example, an exemplary photodynamic therapy device would have essential features of U.S. Pat. No. 6,454,789B1 to Chen et al., which is incorporated in its entirety by this reference; an exemplary thermotherapy device would have essential features of U.S. Pat. No. 6,488,697 to Ariura et al., which is incorporated in its entirety by this reference; an exemplary cryotherapy device would have essential features of U.S. Pat. No. 6,514,245B1 to Williams et al., which is incorporated in its entirety by this reference; and an exemplary electrocautery device would have essential features of U.S. Pat. No. 6,156,035 to Songer, which is incorporated in its entirety by this reference. The syringe system may alternatively be configured for sealing a bleb, serving as a vehicle for drug administration or air removal from a bleb, etc. Therefore, it would be within the capacity of one of ordinary skill in the relevant medical device art to adapt such utility instruments for use with or as an integrated component of the present invention without undue experimentation.

With respect to the bioactive product, it may be a variety of therapeutic substances, but for chemotherapeutic indications, it may comprise a wide variety of chemotherapeutic agents such as but not limited to the exemplary chemotherapeutic agents like cis-platinum, paclitaxol, 5-flourouracial, gemcytobine and navelbine. The chemotherapeutic agents are generally grouped as DNA-interactive Agents, Antimetabolites, Tubulin-Interactive Agents, Hormonal agents and others such as Asparaginase or Hydroxyurea. Each of the groups of chemotherapeutic agents can be further divided by type of activity or compound. The chemotherapeutic agents used in combination with the anti-cancer agents or benzimidazoles of this invention include members of all of these groups. For a detailed discussion of the chemotherapeutic agents and their method of administration, see Dorr, et al, *Cancer Chemotherapy Handbook, 2d edition*, pages 15-34, Appleton & Lange (Connecticut, 1994) herein incorporated by this reference.

DNA-Interactive Agents include the alkylating agents, e.g. Cisplatin, Cyclophosphamide, Altretamine; the DNA strand-breakage agents, such as Bleomycin; the intercalating topoisomerase II inhibitors, e.g., Dactinomycin and Doxorubicin); the nonintercalating topoisomerase II inhibitors such as, Etoposide and Teniposide; and the DNA minor groove binder Plicamycin. The alkylating agents form covalent chemical adducts with cellular DNA, RNA, and protein molecules and with smaller amino acids, glutathione and similar chemicals. Generally, these alkylating agents react with a nucleophilic atom in a cellular constituent, such as an amino, carboxyl, phosphate, or sulfhydryl group in nucleic acids, proteins, amino acids, or glutathione. The mechanism and the role of these alkylating agents in cancer therapy are not well understood. Typical alkylating agents include: Nitrogen mustards, such as Chlorambucil, Cyclophosphamide, Isofamide, Mechlorethamine, Melphalan, Uracil mustard; aziridines such as Thiotepa; methanesulfonate esters such as Busulfan; nitroso ureas, such as Cannustine, Lomustine, Streptozocin; platinum complexes, such as Cisplatin, Carboplatin; bioreductive alkylator, such as Mitomycin, and Procarbazine, Dacarbazine and Altretamine; DNA strand breaking agents include Bleomycin; DNA topoisomerase II inhibitors include the following: Intercalators, such as Amsacrine, Dactinomycin, Daunorubicin, Doxorubicin, Idarubicin, and Mitoxantrone; nonintercalators, such as Etoposide and Teniposide. The DNA minor groove binder is Plicamycin.

The Antimetabolites interfere with the production of nucleic acids by one or the other of two major mechanisms. Some of the drugs inhibit production of the deoxyribonucleoside triphosphates that are the immediate precursors for DNA synthesis, thus inhibiting DNA replication. Some of the compounds are sufficiently like purines or pyrimidines to be able to substitute for them in the anabolic nucleotide pathways. These analogs can then be substituted into the DNA and RNA instead of their normal counterparts. The Antimetabolites useful herein include: folate antagonists such as Methotrexate and trimetrexate pyrimidine antagonists, such as Fluorouracil, Fluorodeoxyuridine, CB3717, Azacytidine, Cytarabine, and Floxuridine purine antagonists include Mercaptopurine, 6-Thioguanine, Fludarabine, Pentostatin; sugar modified analogs include Cyctrabine, Fludarabine; ribonucleotide reductase inhibitors include Hydroxyurea.

Tubulin Interactive agents act by binding to specific sites on Tubulin, a protein that polymerizes to form cellular microtubules. Microtubules are critical cell structure units. When the interactive agents bind on the protein, the cell cannot form microtubules Tubulin Interactive agents include Vincristine and Vinblastine, both alkaloids and Paclitaxel.

Hormonal agents are also useful in the treatment of cancers and tumors. They are used in hormonally susceptible tumors and are usually derived from natural sources. These include: estrogens, conjugated estrogens and Ethinyl Estradiol and Diethylstilbestrol, Chlorotrianisene and Idenestrol; progestins such as Hydroxyprogesterone caproate, Medroxyprogesterone, and Megestrol; androgens such as testosterone, testosterone propionate; fluoxymesterone, methyltestosterone; Adrenal corticosteroids are derived from natural adrenal cortisol or hydrocortisone. They are used because of their anti-inflammatory benefits as well as the ability of some to inhibit mitotic divisions and to halt DNA synthesis. These compounds include Prednisone, Dexamethasone, Methylprednisolone, and Prednisolone.

Leutinizing hormone releasing hormone agents or gonadotropin-releasing hormone antagonists are used primarily the treatment of prostate cancer. These include leuprolide acetate and goserelin acetate. They prevent the biosynthesis of steroids in the testes.

Antihormonal antigens include antiestrogenic agents such as Tamosifen, antiandrogen agents such as Flutamide; and antiadrenal agents such as Mitotane and Aminoglutethimide. Hydroxyurea appears to act primarily through inhibition of the enzyme ribonucleotide reductase. Asparaginase is an enzyme that converts asparagine to nonfunctional aspartic acid and thus blocks protein synthesis in the tumor. It should also be noted that the bioactive product may include as much as about 99.9% chemotherapeutic agent to as little as <1% chemotherapeutic agent or any amount there between.

It should be noted as well that the present device can be used to remove suitable bifurcated stents from lumen. For example, preferred stents as described above, have retrieval means such as suture apertures about the proximal rim of the primary lumen 201, and in alternative embodiments at the right 202 and left 203 branch lumens as well. Other suitable retrieval means would include but are not limited to various stent lumen radius reducing methods such as the one disclosed in co-pending PCT patent application number PCT/DE02/01244 which is incorporated in its entirety by this reference. Alternatively, the ambient temperature may be modified about the stent using cryotherapeutic or thermotherapeutic utility instruments to encourage the stent to relax its deployed configuration and assume a less rigid form. Suitable retrieval tools may be passed through the utility channels 350 to install and/or grasp the suture, which allows the stent to sufficiently collapse for removal. As discussed above, suitable removable stents may have alternative retrieval means such as, but not limited to, lumen diameter reducing wire structures, catch elements etc.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes, which come within the meaning and range of equivalency of the claims, are to be embraced within their scope.

What is claimed is:

1. A device for allowing a user to deploy a bifurcated stent having left and right branches in an anatomical lumen of a patient, the device comprising:
    a longitudinally extending inner tubular member having distal and proximal ends, the inner tubular member defines a lumen longitudinally extending substantially the distance from the distal end to the proximal end of the inner tubular member and forming a longitudinal expanse there between, the longitudinal expanse forming an aperture there through;
    a bifurcated stent retainer coupled to the inner tubular member and having proximal and distal ends, wherein the proximal end of the bifurcated stent retainer is coupled to the distal end of the inner tubular member such that the bifurcated stent retainer extends distally of the distal end of the inner tubular member, wherein the bifurcated stent retainer has a generally frustroconical portion configured to enclose both of the left and right branches of the bifurcated stent therein;
    a longitudinally extending outer tubular member having an exterior and interior diameter, the outer tubular member being longitudinally and axially displaceable relative to the inner tubular member and the bifurcated stent retainer; and
    a handle, coupled with a portion of the outer tubular member.

2. The device of claim 1, wherein the inner tubular member has a pusher coupled with a portion of the inner tubular member for urging egress of a stent from the bifurcated stent retainer.

3. The device of claim 1, wherein the bifurcated stent retainer has a perforation formed on a portion thereof that is configured to facilitate separation of the bifurcated stent retainer for deploying the bifurcated stent.

4. The device of claim 3, wherein the perforation extends proximally from a distal end of the bifurcated stent retainer such that the distal end of the bifurcated stent retainer may separate along the perforation.

5. The device of claim 1, wherein the outer tubular member has longitudinally extending channels extending substantially between the distal and proximal ends thereof.

6. The device of claim 5, wherein the longitudinally extending channels accommodate utility instruments through a lumen thereof 7. The device of claim 6, wherein the utility instrument comprises a guidewire.

8. The device of claim 1, wherein the outer tubular member has longitudinally extending channels that do not extend the entire distance between the distal and proximal ends thereof.

9. The device of claim 8, wherein the longitudinally extending channels accommodate utility instruments through a lumen thereof.

10. The device of claim 1, wherein the bifurcated stent retainer extends distally of the distal end of the inner tubular member when enclosed by the outer tubular member.

11. A device for allowing a user to deploy a bifurcated stent having left and right branches in an anatomical lumen of a patient, the device comprising:
    a longitudinally extending inner tubular member having distal and proximal ends, the inner tubular member defines a lumen longitudinally extending substantially the distance from the distal end to the proximal end of the inner tubular member and forming a longitudinal expanse therebetween, the longitudinal expanse forming an aperture there through;
    a bifurcated stent retainer coupled to the inner tubular member, wherein the bifurcated stent retainer comprises a perforation that is configured to facilitate separation of the bifurcated stent retainer for deploying the bifurcated stent wherein the bifurcated stent retainer has a generally frustroconical portion configured to enclose both the left and right branches of the bifurcated stent therein;

a longitudinally extending outer tubular member having an exterior and interior diameter, the outer tubular member being longitudinally and axially displaceable relative to the inner tubular member and the bifurcated stent retainer, wherein the outer tubular member is configured to overlie the bifurcated stent retainer such that retraction of the outer tubular member releases the stent such that the stent is configured to expand and apply an outward radial force on the bifurcated stent retainer thereby directly resulting in separation of the perforation; and a handle, coupled with a portion of the outer tubular member.

12. The device of claim 11, wherein the perforation extends proximally from the distal end of the bifurcated stent retainer such that the distal end may separate along the perforation.

13. The device of claim 11, wherein the bifurcated stent retainer is configured to enclose both of the left and right branches of the bifurcated stent therein.

14. The device of claim 11, wherein the bifurcated stent retainer has proximal and distal ends, and wherein the proximal end of the bifurcated stent retainer is coupled to the distal end of the inner tubular member such that the inner tubular member and bifurcated stent retainer are not axially displaceable with respect to one another.

15. The device of claim 11, wherein retraction of the outer tubular member is configured to release the left and right branches of the bifurcated stent at approximately the same time.

16. A device for allowing a user to deploy a bifurcated stent having left and right branches in an anatomical lumen of a patient, the device comprising:

a longitudinally extending inner tubular member having distal and proximal ends, the inner tubular member defines a lumen longitudinally extending substantially the distance from the distal end to the proximal end of the inner tubular member and forming a longitudinal expanse therebetween, the longitudinal expanse forming an aperture there through;

a bifurcated stent retainer having proximal and distal ends, the proximal end of the bifurcated stent retainer coupled to the distal end of the inner tubular member such that the inner tubular member and bifurcated stent retainer are not axially displaceable with respect to one wherein the bifurcated stent retainer has a generally frustroconical portion configured to enclose both of the left and right branches of the bifurcated stent therein;

a longitudinally extending outer tubular member having an exterior and interior diameter, the outer tubular member being longitudinally and axially displaceable relative to the inner tubular member and the bifurcated stent retainer; and a handle, coupled with a portion of the outer tubular member.

17. The device of claim 16, wherein the bifurcated stent retainer comprises a perforation extending proximally from its distal end such that the distal end of the bifurcated stent retainer may separate along the perforation.

18. The device of claim 16, wherein the outer tubular member is configured to overlie the bifurcated stent retainer such that retraction of the outer tubular member releases the stent such that the stent is configured to expand and apply an outward radial force on the bifurcated stent retainer thereby directly resulting in separation of the perforation.

* * * * *

UNITED STATES PATENT AND TRADEMARK OFFICE
CERTIFICATE OF CORRECTION

PATENT NO. : 7,604,660 B2  
APPLICATION NO. : 10/427539  
DATED : October 20, 2009  
INVENTOR(S) : Borg et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 438 days.

Signed and Sealed this

Fourteenth Day of December, 2010

David J. Kappos
*Director of the United States Patent and Trademark Office*